US009072820B2

(12) United States Patent
Gale et al.

(10) Patent No.: US 9,072,820 B2
(45) Date of Patent: Jul. 7, 2015

(54) POLYMER COMPOSITE STENT WITH POLYMER PARTICLES

(75) Inventors: David C. Gale, San Jose, CA (US); Yunbing Wang, Mountain View, CA (US)

(73) Assignee: ADVANCED CARDIOVASCULAR SYSTEMS, INC., Santa Clara, CA (US)

( * ) Notice: Subject to any disclaimer, the term of this patent is extended or adjusted under 35 U.S.C. 154(b) by 913 days.

(21) Appl. No.: 11/475,434

(22) Filed: Jun. 26, 2006

(65) Prior Publication Data

US 2007/0299504 A1    Dec. 27, 2007

(51) Int. Cl.
 *A61F 2/82* (2013.01)
 *A61L 27/48* (2006.01)
 *A61L 31/12* (2006.01)

(52) U.S. Cl.
 CPC ............... *A61L 27/48* (2013.01); *A61L 31/129* (2013.01)

(58) Field of Classification Search
 None
 See application file for complete search history.

(56) References Cited

U.S. PATENT DOCUMENTS

| | | | |
|---|---|---|---|
| 3,687,135 A | 8/1972 | Stroganov et al. | |
| 3,839,743 A | 10/1974 | Schwarcz | |
| 3,900,632 A | 8/1975 | Robinson | |
| 4,097,549 A * | 6/1978 | Kruse | 525/86 |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,800,882 A | 1/1989 | Gianturco | |
| 4,816,339 A | 3/1989 | Tu et al. | |
| 4,818,559 A | 4/1989 | Hama et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,902,289 A | 2/1990 | Yannas | |
| 4,916,193 A * | 4/1990 | Tang et al. | 525/413 |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,080,665 A * | 1/1992 | Jarrett et al. | 606/219 |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,104,410 A | 4/1992 | Chowdhary | |
| 5,108,417 A | 4/1992 | Sawyer | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |
| 5,282,860 A | 2/1994 | Matsuno et al. | |
| 5,289,831 A | 3/1994 | Bosley | |
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A * | 8/1994 | Jarrett et al. | 606/219 |
| 5,342,621 A | 8/1994 | Eury | |

(Continued)

FOREIGN PATENT DOCUMENTS

DE    44 07 079    9/1994
DE    197 31 021   1/1999

(Continued)

OTHER PUBLICATIONS

Bates Science 1991 251:898-905.*
Slivka et al. Tissue Engineering 2001 7:767-780.*
Odian Principles of Polymerization New York:John Wiley and Sons, Inc. 1991 p. 24.*
Kwon et al. Journal of Biomaterial Science Polymer Edition 2001 12:1147-1160.*
Campbell et al. Journal of Polymer Science Polymer Physics Edition 1980 18:83-93.*
Na et al., Biomacromolecules vol. 3, pp. 1179-1186, publication year: 2002.*
U.S. Appl. No. 10/317,435, filed Dec. 11, 2002, Hossainy et al.
Anonymous, *Bioabsorbable stent mounted on a catheter having optical coherence tomography capabilities*, Research Disclosure, Sep. 2004, pp. 1159-1162.

(Continued)

*Primary Examiner* — Johann R Richter
*Assistant Examiner* — Katherine Peebles
(74) *Attorney, Agent, or Firm* — Squire Patton Boggs (US) LLP

(57) ABSTRACT

Polymer composite implantable medical devices, such as stents, and methods of manufacturing such devices are disclosed.

20 Claims, 2 Drawing Sheets

(56) References Cited

U.S. PATENT DOCUMENTS

| | | | |
|---|---|---|---|
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A * | 6/1998 | Turnlund et al. ............ 623/1.15 |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,146,655 A * | 11/2000 | Ruben ............................ 424/443 |
| 6,150,630 A | 11/2000 | Perry et al. |
| 6,153,252 A | 11/2000 | Hossainy et al. |
| 4,776,337 B1 | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |

(56) References Cited

U.S. PATENT DOCUMENTS

| | | |
|---|---|---|
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,511 B1* | 1/2003 | Slivka et al. ............... 623/23.75 |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,783,712 B2* | 8/2004 | Slivka et al. .................... 264/51 |
| 6,818,063 B1 | 11/2004 | Kerrigan |
| 6,846,323 B2 | 1/2005 | Yip et al. |
| 7,070,615 B1* | 7/2006 | Igaki ........................... 623/1.15 |
| 7,687,098 B1* | 3/2010 | Chi ............................. 427/2.26 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0074696 A1 | 6/2002 | Wu et al. |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105245 A1* | 6/2003 | Amsden ........................ 525/450 |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1* | 11/2003 | Penhasi ........................ 623/1.15 |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |
| 2005/0038498 A1* | 2/2005 | Dubrow et al. ............... 623/1.15 |
| 2005/0276841 A1* | 12/2005 | Davis et al. ................... 424/443 |
| 2006/0178748 A1* | 8/2006 | Dinger et al. ............... 623/18.11 |
| 2007/0050018 A1* | 3/2007 | Wainwright .................. 623/1.51 |
| 2007/0132155 A1* | 6/2007 | Burgermeister et al. ...... 264/479 |
| 2007/0149641 A1* | 6/2007 | Goupil et al. ................. 523/116 |

FOREIGN PATENT DOCUMENTS

| | | |
|---|---|---|
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| EP | 1 607 109 | 12/2005 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO99/11296 * | 3/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO01/67990 * | 9/2001 |
| WO | WO 2004/023985 | 3/2004 |

OTHER PUBLICATIONS

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

(56) References Cited

OTHER PUBLICATIONS

Casper et al., *Fiber-Reinforced Absorbable Composite for Orthopedic Surgery*, Polymeric Materials Science and Engineering, vol. 53 pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules, vol. 2, pp. 430-441 (2001).
Hahn et al., *Biocompatibility of Glow-Discharge-Polymerized Films and Vacuum-Deposited Parylene*, J Applied Polymer Sci, vol. 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Kelley et al., *Totally Resorbable High-Strength Composite Material*, Advances in Biomedical Polymers, vol. 35, pp. 75-85 (1987).
Kubies et al., *Microdomain Structure in polylactide-block-poly(ethylene oxide) copolymer films*, Biomaterials, vol. 21, pp. 529-536 (2000).
Kutryk et al., *Coronary Stenting: Current Perspectives*, a companion to the Handbook of Coronary Stents, p. 1-16 (1999).
Martin et al., *Enhancing the biological activity of immobilized osteopontin using a type-1 collagen affinity coating*, J. Biomed. Mater. Res., vol. 70A, pp. 10-19 (2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., vol. 1(4), pp. 438-448 (Jul./Aug. 1990).
Nichols et al., *Electrical Insulation of Implantable Devices by Composite Polymer Coatings*, ISA Transactions, vol. 26(4), pp. 15-18 (1987).
Peuster et al., *A novel approach to temporary stenting: degradable cardiovascular stents produced from corrodible metal-results 6-18 months after implantation into New Zealand white rabbits*, Heart, vol. 86, pp. 563-569 (2001).
Pietrzak et al., *Bioabsorbable Fixation Devices: Status for the Craniomaxillofacial Surgeon*, J. Craniofaxial Surg., vol. 2, pp. 92-96 (1997).
Pietrzak et al., *Bioresorbable implants—practical considerations*, Bone, vol. 19, No. 1, Supplement Jul. 1996, pp. 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, vol. 79(2), pp. 445-457 (Feb. 1989).
Schmidt et al., *Long-Term Implants of Parylene-C Coated Microelectrodes*, Med & Biol Eng & Comp, vol. 26(1), pp. 96-101 (Jan. 1988).
Spagnuolo et al., *Gas 1 is induced by VE-cadherin and vascular endothelial growth factor and inhibits endothelial cell apoptosis*, Blood, vol. 103, pp. 3005-3012 (2004).
Tamai et al., *Initial and 6-Month Results of Biodegradable Poly-l-Lactic Acid Coronary Stents in Humans*, Circulation, pp. 399-404 (Jul. 25, 2000).
Tsuji et al., *Biodegradable Polymeric Stents*, Current Interventional Cardiology Reports, vol. 3, pp. 10-17 (2001).
Zhang et al., *The effect of elastomeric nano-particles on the mechanical properties and crystallization behavior of polypropylene*, Polymer, 43, pp. 5133-5138 (2002).
Völkel et al., *Targeting of immunoliposomes to endothelial cells using a single—chain Fv fragment directed against human endoglin (CD105)*, Biochimica et Biophysica Acta 1663, pp. 158-166 (2004).
von Recum et al., *Degradation of polydispersed poly(L-lactic acid) to modulate lactic acid release*, Biomaterials, vol. 16, pp. 441-445 (1995).
Yau et al., Modern Size-Exclusion Liquid Chromatography, Wiley-Interscience Publication, IX-XV (1979).
International Search Report for PCT/US2007/014571, mailed Jul. 14, 2008, 7 pgs.

* cited by examiner

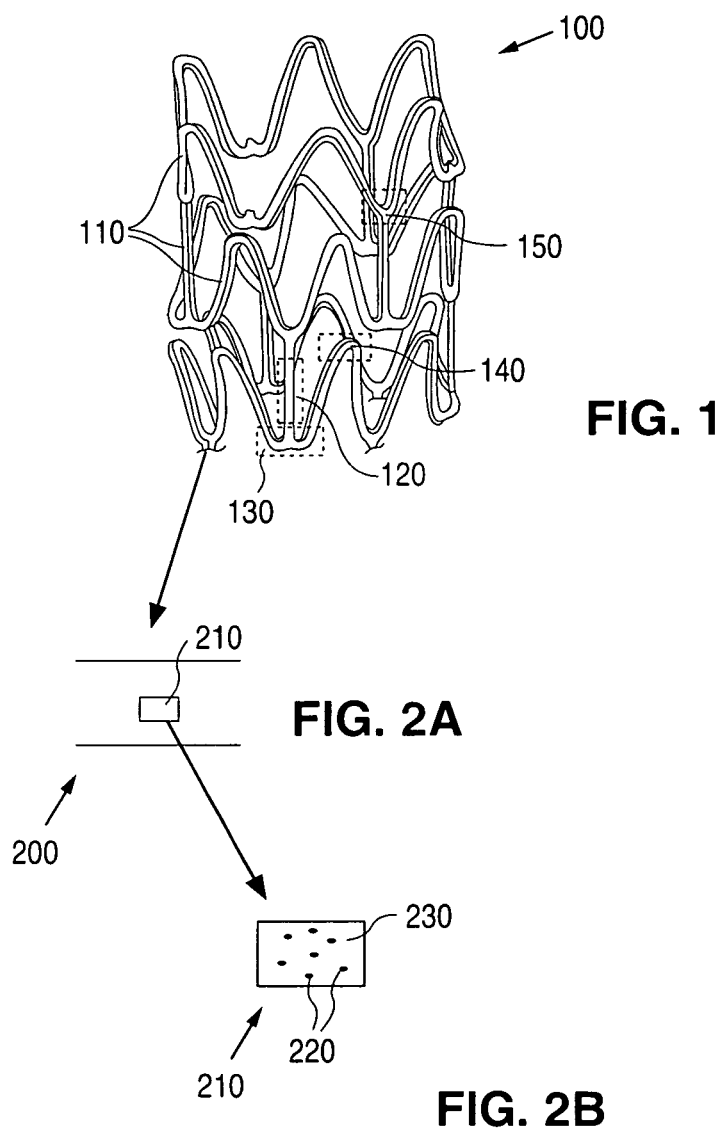

POLYMER COMPOSITE STENT WITH POLYMER PARTICLES

BACKGROUND OF THE INVENTION

1. Field of the Invention

This invention relates to polymer composite implantable medical devices, such as stents, with polymer particles.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthemiore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

However, some biodegradable polymers having sufficient strength and modulus for use as stent materials, but do not have the toughness desired for or required of a stent. Such biodegradable polymers tend to be brittle under physiological conditions or conditions within a human body. Additionally, some biodegradable polymers have degradation rates that are slower than desired.

SUMMARY OF THE INVENTION

Certain embodiments of the present invention include an implantable medical device comprising a structural element, the structural element including a composite, the composite having a plurality of polymer particles dispersed within a polymer matrix, wherein the particle polymer has a lower modulus than the matrix polymer, and wherein the composite comprises a higher toughness than the matrix polymer.

Further embodiments of the present invention include a method of fabricating an implantable medical device comprising: mixing a plurality of crosslinked polymer particles with a matrix polymer above the Tm of the matrix polymer, wherein the particle polymer has a lower modulus than the matrix polymer; forming a polymer construct from the mixture; and fabricating an implantable medical device from the construct.

Additional embodiments of the present invention include a method of fabricating an implantable medical device comprising: mixing a particle polymer with a matrix polymer above the Tm of the particle polymer and the Tm of the matrix polymer such that the particle polymer and matrix polymer are polymer melts, wherein the mixing causes the particle polymer to form a plurality of discrete particulate domains dispersed within the matrix polymer, and wherein the particle polymer has a lower modulus than the matrix polymer; forming a polymer construct from the mixture, the polymer construct comprising the discrete particulate domains dispersed with the matrix polymer; and fabricating an implantable medical device from the construct.

BRIEF DESCRIPTION OF THE DRAWINGS

FIG. 1 depicts a stent.

FIG. 2A depicts a section of a structural element from the stent depicted in FIG. 1.

FIG. 2B depicts particles dispersed within a polymer matrix.

DETAILED DESCRIPTION OF THE INVENTION

Figure 3A:
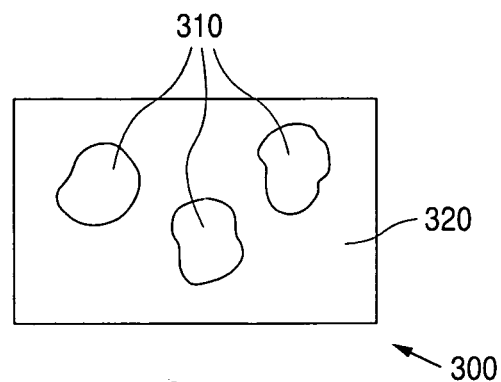
FIG. 3A depicts a schematic view of a portion of a polymer melt mixture prior to nanoparticle or microparticle phase separation.

The various embodiments of the present invention relate to composite polymer implantable medical devices and methods of fabricating composite polymer stents having strength, modulus, and toughness sufficiently high for treating a bodily lumen. Embodiments of the composite polymer implantable medical have a structural element including a plurality of polymer particles dispersed within a matrix polymer, the particle polymer having a lower modulus than the matrix polymer. In some embodiments, the particles are composed of an elastomeric or rubbery polymer.

The present invention can be applied to implantable medical devices including, but is not limited to, self-expandable stents, balloon-expandable stents, stent-grafts, and grafts (e.g., aortic grafts), implantable cardiac pacemakers and defibrillators, leads and electrodes for the preceding, implantable organ stimulators such as nerve, bladder, sphincter and diaphragm stimulators, cochlear implants, prostheses, vascular grafts, artificial heart valves, and cerebrospinal fluid shunts.

In particular, a stent can have a scaffolding or a substrate that includes a pattern of a plurality of interconnecting structural elements or struts. FIG. 1 depicts an example of a view of a stent 100. Stent 100 may be formed from a tube (not shown). Stent 100 includes a pattern of structural elements 110, which can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited.

Implantable medical devices can be formed from a construct such as a tube, sheet, or other shape or form. A polymer construct, for instance, may be formed by methods such as extrusion or injection molding. A stent such as stent 100 may be fabricated from a polymeric tube or a sheet by rolling and bonding the sheet to form a tube. A stent pattern may be formed on a polymer tube by laser cutting a pattern on the tube. Representative examples of lasers that may be used include, but are not limited to, excimer, carbon dioxide, and YAG. In other embodiments, chemical etching may be used to form a pattern on a tube.

The geometry or shape of an implantable medical device may vary throughout its structure to allow radial expansion and compression. A pattern may include portions of structural elements or struts that are straight or relatively straight, an example being a portion 120. In addition, patterns may include structural elements or struts that include bending elements such as portions 130, 140, and 150. Bending elements bend inward when a stent is crimped and outward when a stent is radially expanded. After deployment, a stent is under static and cyclic compressive loads from the vessel walls. Thus, the curved portions of the bending elements are subjected to relatively high stress and strain during use.

Therefore, a stent has certain mechanical requirements that include a sufficiently high modulus, strength, and toughness. A stent must have have a sufficiently high modulus to resist recoil inward as it supports a bodily lumen. A stent should also have sufficient radial strength to withstand the structural loads, namely radial compressive forces, imposed on the stent as it supports the walls of a vessel. A stent should have toughness sufficient to resist fracture at the magnitude of the loads and degree of strain imposed on the stent during and after deployment.

"Toughness" is defined as the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness since it has a tendency to fracture at a relatively low level of strain with little or no plastic deformation.

Some polymers, in particular biodegradable polymers, such as poly(L-lactide) (PLLA), have sufficiently high strength and modulus for stent applications, but have insufficient toughness under physiological conditions or conditions within a human body. These polymer systems tend to exhibit a brittle fracture mechanism in which there is little or no plastic deformation prior to failure. Such polymers can have a Tg above human body temperature which is approximately 37° C.

Another deficiency of some biodegradable polymers, such as PLLA, is that the degradation rate is relatively slow and results in a degradation time of a stent outside of a desired range. Degradation time refers to the time for an implantable medical device to substantially or completely erode away from an implant site. It is generally desirable for a stent to disintegrate and disappear from the region of implantation once treatment is completed. For stents made from a biodegradable polymer, the stent is intended to remain in the body for a duration of time until its intended function of, for example, maintaining vascular patency and/or drug delivery is accomplished. The duration of a treatment period depends on the bodily disorder that is being treated. For illustrative purposes only, the duration can be up to a month, three months, six months, twelve months, eighteen months, or two years.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind.

The degradation time of a slow eroding polymer can be decreased by increasing the degradation rate. The degradation rate may be characterized by, for example, the average erosion rate or the half-life of a polymer. The "average erosion rate" may be an average erosion or mass loss rate over any selected time interval:

$$\text{Average erosion rate} = (m_2 - m_1)/(t_2 - t_1)$$

where "m" refers to mass of the device, "t" refers to a time during erosion, and $m_1$ and $m_2$ are the masses of the device at $t_1$ and $t_2$ during erosion. For instance, the selected time interval may be between the onset of degradation and another selected time. Other selected times, for example, may be the time for about 25%, 50%, 75%, or 100% (complete erosion) of the device to erode. The time for complete erosion may correspond approximately to the duration of treatment. The "half-life" of a degrading polymer refers to the length of time for the molecular weight of the polymer to fall to one half of its original value. See e.g., J. C. Middleton and A. J. Tipton, Biomaterials, Vol. 21 (23) (2000) pp. 2335-2346.

Various embodiments of the present invention include an implantable medical device fabricated from a composite including a polymer matrix or continuous phase and polymer particles as a discrete phase. The particles are expected to enhance the fracture toughness of a device while maintaining a sufficiently high strength and modulus of the device.

In some embodiments, the matrix polymer is a biodegradable polymer. The particles can also be degradable. Thus, in addition to enhancing toughness of the matrix polymer, the particles can decrease the degradation time of the device by increasing the degradation rate of the matrix polymer.

In certain embodiments, a structural element of an implantable medical device may be composed of, formed from, or fabricated from a composite. The composite can have a plurality of polymeric particles dispersed within a polymer matrix. In one exemplary embodiment, the matrix polymer can be PLLA.

Structural elements can include, but are not limited to, any element that makes up the structure of the device such as a strut, wire, or filament. FIG. 2A depicts a section 200 of a structural element 110 from stent 100. A portion 210 of section 200 is shown in an expanded view in FIG. 2B. FIG. 2B depicts particles 220 dispersed throughout a polymer matrix 230.

In some embodiments, the matrix polymer can be a polymer with a relatively low fracture toughness and that is brittle at physiological conditions. In an embodiment, the matrix polymer is a semicrystalline polymer. Additionally, the particle polymer can be selected so that it has a lower modulus and higher toughness than the matrix polymer. For example, the particle polymer can have a modulus that is 10%, 30%, 50%, 70%, or 80% of the matrix polymer.

In an embodiment, the particle polymer can be an elastomeric or rubbery polymer. An "elastomer" or "rubbery" polymer refers to a polymer which can resist and recover from deformation produced by force, as in natural rubber. In one embodiment, at room temperature, elastomers or rubbery polymers can be stretched repeatedly to at least twice their original length and, immediately upon release of the stress, return with force to their approximate original length. In another embodiment, elastomers are amorphous polymers existing above their glass transition temperature.

In certain embodiments, the particles can be composed of in whole or part of a crosslinked polymer. Such particles can be pre-formed and combined with a matrix polymer during processing of the composite, which is described below.

In another embodiment, the particles can be a non-crosslinked polymer. In one embodiment, the non-crosslinked polymer can be immiscible with the matrix polymer to allow particles to be formed within the matrix polymer through microphase separation during processing, which is described below. "Immiscible" refers to the inability of a mixture of the polymers to form a single phase in the ranges of composition of the mixture and in the ranges of temperature and pressure at (1) ambient conditions (1 atm, 15° C. to 30° C.), (2) during processing of the composite and device, and (2) at physiological conditions.

In some embodiments, the non-crosslinked polymer particles can be miscible with the matrix polymer. "Miscible" refers to the cability of a mixture of the polymers to form a single phase in the ranges of composition of the mixture and in the ranges of temperature and pressure at (1) ambient conditions (1 atm, 15° C. to 30° C.), (2) during processing of the composite and device, and (2) at physiological conditions. In such an embodiment, the melting temperature (Tm) of the non-crosslinked polymer can be greater than the particle polymer to allow melt blending of the particles with a matrix polymer. In particular, a composite can be formed by blending the non-crosslinked particle with a matrix polymer at a temperature above the Tm of the matrix polymer and below the Tm of the particle polymer.

Representative polymers that may be used as a particle polymer include, but are not limited to, poly(butadiene), poly (butadiene-co-acrylonitrile), poly(butadiene-co-styrene), poly(chloroprene), poly(isobutene-co-isoprene), ethylene-propylene-diene-terpolymer, poly(butyl acrylate), poly(vinylidene fluoride-co-hexafluoropropylene), epichlorohydrin rubber, polyacrylic rubber, chlorosulfonated polyethylene, silicone, fluorosilicone, polyurethane, resilin, polyamide, poly(glycerol sebacate), poly(trimethylene carbonate), poly (caprolactone), poly(lactide-co-trimethylene carbonate), poly(glycolide-co-trimethylene carbonate), poly(glycolic acid-co-trimethylene carbonate)-block-polylactide, poly (lactide-co-ε-caprolactone), poly(glycolide-co-caprolactone), and poly(hydroxybutyrate-co-caprolactone).

Various sizes of the particles may be used in the composite. For example, the particles can include, but are not limited to, nanoparticles and microparticles. A nanoparticle refers to a particle with a characteristic length (e.g., diameter) in the range of about 1 nm to about 1,000 nm. In some embodiments, the characteristic length of the nanoparticles can be less than 100 nm. In other embodiments, the characteristic length of the nanoparticles can be less than 300 nm, 500 nm, 700 nm, or less than 900 nm. A microparticle refers to a particle with a characteristic length greater than 1,000 nm and less than about 10 microns.

Additionally, particles can be of various shapes. For example, the particles can be spherical, oblong, long fibers, or short fibers.

The composite of a structural element of a device may have less 5 wt %, 3 wt %, 2 wt %, or more narrowly less than 1 wt % of particles as compared to the matrix polymer of the composite.

Additionally, in some embodiments, matrix polymer crystalline domains may be formed adjacent to or around the particles. During formation of the composite, as described below, the particles can act as nucleating agents, resulting in the matrix polymer crystallizing adjacent to or around the particles. The crystallites may be dispersed throughout an amorphous domain of the matrix polymer in the composite.

It is generally known to a person of skill in the art that the toughness of a polymer can be enhanced by blending the polymer with a low modulus, elastomeric, rubbery material. A problem with this approach, as far as stent applications are concerned, is that the low modulus materials tend to reduce the modulus of the material. The decrease in modulus is directly proportional to the volume of added elastomeric material. Therefore, when enhancing the toughness in this way, it is desirable to achieve a balance between a toughness and stiffness.

It has been shown that the toughness of polypropylene (PP) is increased substantially by the blending elastomeric nanoparticles with the polypropylene. Zhang M, et al., Polymer, 43(2002) 5133-5138. The toughness of the PP was enhanced even at a level as low as 2 wt % of elastomeric nanoparticles. Ibid. In spite of the presence of the low modulus elastomeric nanoparticles, the PP blends retained and even possessed a slight enhancement in stiffness. Ibid.

It is believed that the retained or enhanced stiffness of the PP blends is due in part to the fact that the elastomeric nanoparticles act not only as a toughening modifier, but as a nucleation agent that speeds up the crystallization kinetics for the PP. Ibid. The increase in the crystallization rate, crystallinity, and nucleation density may act to increase the stiffness of the PP blend, compensating for the decrease in strength and modulus due to the low modulus elastomeric particles. Ibid. Thus, it is expected that the toughness of polymers having strength and modulus suitable for stent applications, such as PLLA, can be enhanced using low modulus particles, such as elastomeric or rubbery particles, while retaining sufficient stiffness and strength.

It is believed that the mechanism of the increase in toughness is due to particles absorbing energy due to applied stress which disperses energy about a larger volume in a composite. Dispersion of the energy is particularly important in high strain regions of the bending regions of a stent. Rather than being highly concentrated the stress and strain in a device fabricated from a composite is divided into many small interactions involving numerous individual particles. When a crack is initiated in the material and starts traveling through the composite, the crack breaks up into finer and finer cracks due to interaction with the particles. Therefore, the particles tend to dissipate the energy imparted to the device by the applied stress.

In general, at least over a range of particles size, the increase in the toughness is directly proportional to the size of the particles. For a give weight ratio of particles to matrix, as the size of the particles decreases the number of particles dispersed throughout the device per unit volume also increases. Thus, the number of particles to disperse the energy of applied stress to the device increases. Therefore, it is advantageous to use nanoparticles to increase the toughness of the polymer. Furthermore, since small particles such as nanoparticles can increase toughness even at relatively low weight percent, the decrease in strength and modulus due to the low modulus particles is reduced.

Also, the particle size distribution can be important in enhancing toughness of a matrix polymer. Generally, it is expected that a monodisperse, narrow size distribution allows particles to be blended more uniformly resulting in more effective enhancement of toughness. In general, a more uniform the dispersion of the particles results in more uniform properties of the composite and a device fabricated from the composite. For example, a uniform dispersion can result in a uniform increase in toughness and modulus and modification of degradation rate, as described below. In some embodiments, the particles are uniformly or substantially uniformly dispersed within the matrix polymer.

In certain embodiments, biodegradable particles can be used to tune the degradation rate of a matrix polymer that is biodegradable. In particular, the particles can decrease the degradation time of the device by increasing the degradation rate of the matrix polymer.

Several mechanisms may be relied upon for erosion and disintegration of implantable devices which include, but are not limited to, mechanical, chemical breakdown and dissolution. In particular, degradation of polymers involves chemical breakdown involving enzymatic and/or hydrolytic cleavage of a device material due to exposure to bodily fluids such as blood. Hydrolysis is a chemical process in which a molecule is cleaved into two parts by the addition of a molecule of water. Consequently, the degree of degradation in the bulk of a polymer is strongly dependent on the concentration of water in a polymer and the diffusion rate of water into the polymer.

As discussed above, some biodegradable polymers, such as poly(L-lactide), have a degradation rate that is slow and results in a degradation time of a stent outside of a desired range. Increasing the equilibrium content of moisture in a biodegradable polymer that degrades by hydrolysis can increase the degradation rate of a polymer. Various embodiments of the present invention include increasing the equilibrium moisture content in a polymer of a device to accelerate the degradation rate.

In order to decrease the degradation time of a composite device, the particle polymer can have a higher degradation rate or a shorter half-life than the matrix polymer. For example, the particle polymer can have a half-life that is 10%, 30%, 50%, 70%, or 90% of the matrix polymer. In an embodiment, the degradation rate of a composite device can be tuned and/or adjusted to obtain a desired degradation time of the device.

As the particles erode within the polymeric matrix, the porosity of the matrix increases. The increased porosity increases the diffusion rate of moisture through the polymeric matrix, and thus, the equilibrium moisture content of the polymeric matrix. As a result, the degradation rate of the polymer is increased. The porous structure also increases the transport of degradation products out of the matrix, which also increases the degradation rate of the matrix.

In certain embodiments, the degradation time of the device can be tuned or controlled through variables such as the size and shape of particles. The faster the degradation rate of the particle particle polymer, the faster the porosity of the polymer matrix increases which results in a greater increase in the degradation rate of the polymer matrix. Additionally, the size of the particles influence the time for erosion of the particles. The smaller the particles, the faster the erosion of the particles because of the higher surface area per unit mass of particles.

For example, nanoparticles may have a relatively fast erosion rate compared to microparticles. Additionally, elongated particles, such as fibers, may tend to erode faster on a per unit mass basis due to the higher surface area per unit mass of the particle. Also, short fibers may tend to erode faster than longer fibers. Short fibers refer to long fibers than have been cut into short lengths. For example, a length of a short fiber can be substantially smaller than a diameter of a stent. In some embodiments, the short fibers may be less than 0.05 mm long. In other embodiments, the short fibers may be between 0.05 and 8 mm long, or more narrowly between 0.1 and 0.4 mm long or 0.3 and 0.4 mm long.

Furthermore, the size and distribution of pores created by erosion of particles can also influence the degradation rate and time of the polymer matrix. Smaller particles, such as nanoparticles, create a porous network that exposes a larger volume of polymer matrix to bodily fluid than larger particles, like microparticles. As a result the degradation rate of the matrix can be higher when nanoparticles are used rather than microparticles.

Therefore, through appropriate selection of the type of material for the particles and the size and shape of the particles, the device can be designed to have a selected degradation time.

In further embodiments, the degradation products of the particle polymer can cause in increase in the degradation rate of the matrix polymer, and thus a decrease in the degradation time of the device. In an embodiment, degradation products of the particle polymer can be acidic. The increase in degradation rate of a degradable polymer by acidic degradation products is referred to as an autocatalytic effect. This effect can result in an increase in the degradation rate of a matrix polymer that degrades through a hydrolysis reaction. The rate of the hydrolysis reaction tends to increase as the pH decreases. Thus, the increase in the pH due to the acidic degradation products of the particle degradation tends to increase the degradation rate of the matrix polymer. In addition, the acidic degradation product is hydrophilic, which increases the uptake of water into the matrix polymer. The increased uptake of water also increases the degradation rate since the hydrolysis reaction of the matrix polymer has water as a reactant.

For example, the particle polymer can include ester linkages that can degrade through addition of water into a degradation product having an acid group. The matrix polymer can also have ester linkages that degrade by hydrolysis into polymer segments having an acid group. The rate of the matrix polymer degradation reaction can be increased by the decreased pH caused by the degradation product of the particle polymer. The acid group of the degradation product of the particle polymer and the acid group of the matrix polymer segment are hydrophilic which increases the water uptake, further increasing the hydrolysis reactions.

Further embodiments of the invention include formation of a composite and fabrication of an implantable medical device therefrom. As indicated above, a composite including particles dispersed in a polymer matrix can be extruded to form a polymer construct, such as a tube. A stent can then be fabricated from the tube.

For example, in extrusion, a polymer melt is conveyed through an extruder and forced through a die in the shape of a polymer construct. In the case of a tube, a tubular film exits the die. The melt exiting the die is cooled below the Tm of the polymer to form an extruded polymeric construct. An implantable medical device can then be fabricated from the polymer construct. For instance, a polymer tube can be laser cut to form a stent.

In some embodiments, the composite and implantable medical device can be formed by melt blending particles with a matrix polymer melt. Melt blending can be particularly useful in forming composites having particles that are composed of a crosslinked polymer and/or are a polymer with a Tm that is above the Tm of the matrix polymer. In one embodiment, a method of fabricating an implantable medical device can include mixing a plurality of polymeric particles with a matrix polymer melt. The particle polymer can be selected so that it has a Tm above the Tm of the matrix polymer. In an embodiment, the particles are crosslinked. The temperature of the matrix polymer melt during mixing can be less than the Tm of the particles so that particles do not melt during the mixing. The particles can be mixed with the matrix polymer melt using an extruder or batch processing. The mixture of matrix polymer melt and particles can then be forced through a die to form a polymer construct.

Representative examples of extruders include, but are not limited to, single screw extruders, intermeshing co-rotating and counter-rotating twin-screw extruders and other multiple screw masticating extruders.

In one embodiment, the particles can be combined with the matrix polymer in a powdered or granular form prior to melting of the matrix polymer. The particles and matrix polymer can be mixed using mechanical mixing or stirring such as agitation of the particles and polymer in a container or a mixer. The agitated mixture can then be heated to a temperature above the Tm of the matrix polymer in an extruder or using batch processing. The mixture can then be cooled to below the Tm of the matrix polymer to form the composite. For example, polymer melt can be cooled by conveying it through a water bath at a selected temperature. Alternatively, the polymer melt may be cooled by a gas at a selected temperature.

Another embodiment of forming a composite can include melt blending a non-crosslinked polymer with a matrix polymer above the Tm of both the particle polymer and the matrix polymer. To allow for the formation of particles within the matrix polymer, the particle polymer can be immiscible with the matrix polymer. The particles are formed through microphase separation of the discrete phase particle polymer from a continuous phase matrix polymer.

In one embodiment, a particle polymer can be mixed with a matrix polymer, the particle polymer and the matrix polymer being above their Tm's. The particle polymer can be added to the matrix polymer in a form that facilitates blending of the particle polymer and matrix polymer. For example, the particle polymer can be added to the matrix polymer in powdered or granular form. The particle polymer melt and the matrix polymer melt can be mixed so that the particle polymer forms a plurality of discrete particulate domains having nanoparticle or microparticle characteristic lengths dispersed within the matrix polymer.

Figure 3B:
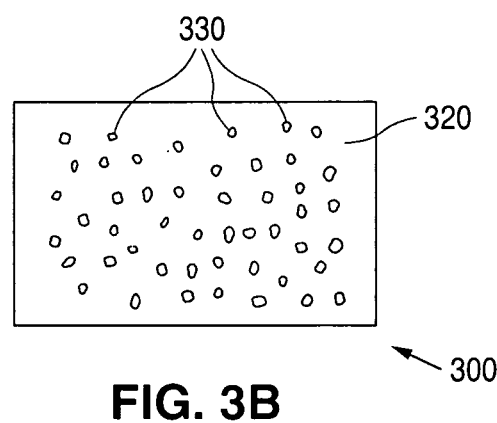
FIG. 3B depicts a portion of a polymer melt with nanoparticle or microparticle phase separation.

FIG. 3A depicts a schematic view of a portion 300 of a polymer melt mixture prior to nanoparticle or microparticle phase separation. Portion 300 in FIG. 3A shows a particle polymer discrete phase 310 dispersed within a matrix polymer continuous phase 320. FIG. 3B depicts portion 300 after mixing causes nanoparticle or microparticle phase separation showing discrete particulate domains 330 of particle polymer dispersed within matrix polymer 320.

Upon cooling the mixture to below the Tm's of the particle polymer and matrix polymer, the resulting mixture or composite can have the discrete particulate domains of nanoparticle or microparticle characteristic lengths dispersed with the matrix polymer. The mixing can be performed, for example, in an extruder or batch processing. Prior to or during cooling, the mixture of matrix polymer melt and particulate domains can be forced through a die to form a polymer construct.

Additionally, a method of forming the polymer construct also include allowing matrix polymer crystallites to form adjacent to or around the particles or discrete particulate domains. The crystallites can be dispersed throughout an amorphous domain of the matrix polymer. The crystallinity, crystal size, and crystal density can be controlled by controlling the temperature of the cooling matrix polymer melt. In general, crystallization in a polymer tends to occur at temperatures between Tg and Tm of the polymer. Therefore, in some embodiments, the temperature of the polymer construct during cooling can be between Tg and Tm of the matrix polymer. As the temperature of the polymer melt is cooled below Tm to form a polymer construct, such as a tube, the particles or particulate domains provide a point of nucleation in the polymer melt for the formation of matrix polymer crystalline domains.

A network of many small crystalline domains is formed, which can work to tie crystalline domains together and reduce, inhibit or prevent fracturing, creep, stress relaxation, and physical aging of the polymer. The crystalline domains can serve as net points in the amorphous domains that restrict the freedom of movement of polymer chains in the amorphous domain. As a result, physical aging, creep, and stress relaxation can be reduced. In addition, as discussed above, the toughness, strength, and modulus of the matrix polymer may be maintained or enhanced by the crystallites.

In general, both microparticles and nanoparticles can be used as nucleation points. However, as the number of particles increases and size of the particles decreases, the crystalline domains become more effective in maintaining or enhancing mechanical properties.

Figure 4:
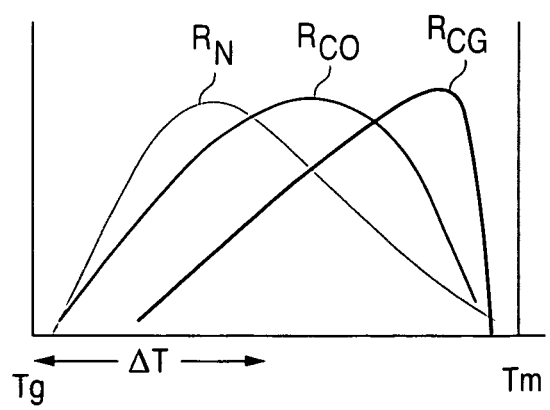
FIG. 4 depicts a schematic plot of the crystal nucleation rate, the crystal growth rate, and the overall rate of crystallization for a semicrystalline polymer.

In certain embodiments, the size of the crystalline domains can be controlled by the temperature of the cooling polymer construct from an extruder. The rate of crystallization in this range varies with temperature. FIG. 4 depicts a schematic plot of the crystal nucleation rate ($R_N$), the crystal growth rate ($R_{CG}$), and the overall rate of crystallization ($R_{CO}$). The crystal nucleation rate is the growth rate of new crystals and the crystal growth rate is the rate of growth of formed crystals. The overall rate of crystallization is the sum of curves $R_N$ and $R_{CG}$.

In certain embodiments, the temperature of the cooling polymer construct can be at a temperature at which the overall crystallization rate is relatively low. At such a temperature, the increase in crystallinity is predominantly due to formation of crystalline domains around the particles, rather than the growth of existing crystals. In some embodiments, the temperature can be in a range in which the crystal nucleation rate is larger than the crystal growth rate. In one embodiment, the temperature can be in a range in which the crystal nucleation rate is substantially larger than the crystal growth rate. For example, the temperature can be where the ratio of the crystal nucleation rate to crystal growth rate is 2, 5, 10, 50, 100, or greater than 100. In another embodiment, the temperature range may be in range, $\Delta T$, shown in FIG. 4, between about Tg to about 0.25(Tm−Tg)+Tg. In an embodiment, the temperature of cooling can be controlled so that the crystallites have a characteristic length of less than 10 microns, 5 microns, or less than 2 microns.

For the purposes of the present invention, the following terms and definitions apply:

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

In general, matrix polymer and particles can be made partially or completely from a biodegradable, bioabsorbable, or biostable polymer. A polymer for use in fabricating a composite implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer in device can be caused by, for example, hydrolysis and metabolic processes.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device comprising a structural element, the structural element including a composite, the composite having a plurality of polymer nanoparticles dispersed within a polymer matrix, wherein each of the polymer nanoparticles is a discrete, single phase within the polymer matrix, wherein the polymer nanoparticles have a lower modulus than the matrix polymer, and wherein the composite comprises a higher toughness than the matrix polymer, wherein the polymer nanoparticles are biodegradable, wherein the polymer matrix is poly(L-lactide) and the nanoparticles comprise less than 5 wt % of the composite.

2. The device of claim 1, wherein the polymer nano-particles comprise a cross-linked polymer.

3. The device of claim 1, wherein the polymer nano-particles increase the toughness of the matrix polymer.

4. The device of claim 1, wherein the polymer nano-particles have a higher degradation rate than the matrix polymer.

5. The device of claim 1, wherein the polymer nano-particles are uniformly dispersed within the polymer matrix.

6. The device of claim 1, wherein the degradation products of the polymer nanoparticles are acidic, the acidic degradation products being capable of increasing the degradation rate of the matrix polymer.

7. The device of claim 1, wherein the polymer nano-particles are immiscible with the matrix polymer.

8. The device of claim 1, wherein the polymer nano-particles comprise a non-crosslinked polymer.

9. The device of claim 1, wherein matrix polymer crystalline domains are formed adjacent to or around the polymer nanoparticles, the crystalline domains being dispersed throughout an amorphous domain of the matrix polymer in the composite, the crystalline domains increase the strength and modulus of the composite.

10. The device of claim 1, wherein the polymer nanoparticles are selected from the group consisting of poly(lactide-co-trimethylene carbonate), poly(glycolide-co-trimethylene carbonate), poly(glycolic acid-co-trimethylene carbonate)-block-polylactide, poly(lactide-co-ε-caprolactone), poly(glycolide-co-caprolactone), and poly(hydroxybutyrate-co-caprolactone).

11. The device of claim 1, wherein the polymer nanoparticles have a half-life selected from the group consisting of 10%, 30%, 50%, 70%, and 90% of the matrix polymer.

12. The device of claim 1, wherein the polymer nanoparticles are less than 100 nm in length if fibrous or less than 100 nm in diameter if spherical.

13. The device of claim 1, wherein the polymer nanoparticles are less than 1000 nm in length if fibrous or less that 1000 nm in diameter of spherical.

14. The device of claim 1, wherein the composite is less than 1 wt % nanoparticles as compared to the matrix polymer.

15. The device of claim 1, wherein the composite is less than 5 wt % nanoparticles as compared to the matrix polymer.

16. An implantable medical device comprising a structural element, the structural element including a composite, the composite having a plurality of polymer nanoparticles dispersed within a polymer matrix, wherein each of the polymer nanoparticles is a discrete, single phase within the polymer matrix, wherein the polymer nanoparticles have a lower modulus than the matrix polymer, and wherein the composite comprises a higher toughness than the matrix polymer, wherein the polymer nanoparticles are biodegradable, wherein the polymer matrix is poly(L-lactide), the device is a stent and the nanoparticles comprise less than 5 wt % of the composite.

17. The device of claim 16, wherein the polymer nanoparticles have a higher degradation rate or lower half-life than the matrix polymer.

18. The device of claim 16, wherein the composite is less than 5 wt % polymer nanoparticles as compared to the matrix polymer.

19. The device of claim 16, wherein the polymer nanoparticles are less than 1000 nm in length if fibrous or less than 1000 nm in diameter if spherical.

20. The device of claim 16, wherein the polymer nanoparticles comprise an elastomeric polymer.

* * * * *